United States Patent [19]

D'Sidocky

[11] 4,163,757
[45] Aug. 7, 1979

[54] BASE MODIFIED CATALYSIS IN THE STYRENATION OF DIPHENYLAMINE

[75] Inventor: Richard M. D'Sidocky, Ravenna, Ohio

[73] Assignee: The Goodyear Tire & Rubber Company, Akron, Ohio

[21] Appl. No.: 960,145

[22] Filed: Nov. 13, 1978

[62] Continuation of Ser. No. 840,440, Oct. 7, 1977, abandoned.

[51] Int. Cl.² ............................................. C07C 85/18
[52] U.S. Cl. ............................... 260/570 R; 260/576
[58] Field of Search ........................... 260/570 R, 576

[56] References Cited

U.S. PATENT DOCUMENTS

| 2,776,994 | 1/1957 | Wolfe | 260/576 |
|---|---|---|---|
| 2,943,112 | 6/1960 | Popoff et al. | 260/576 |
| 3,072,603 | 1/1963 | Tholstrup | 260/576 X |
| 3,452,056 | 6/1969 | Sundholm | 260/570 X |
| 3,496,230 | 2/1970 | Kaplan | 260/576 |
| 3,505,225 | 4/1970 | Wheeler | 260/576 X |
| 3,649,690 | 3/1972 | Wheeler | 260/570 |
| 3,714,257 | 1/1973 | Bayha et al. | 260/576 |
| 3,714,258 | 1/1973 | Bayha et al. | 260/576 |

FOREIGN PATENT DOCUMENTS

| 895973 | 10/1953 | Fed. Rep. of Germany | 260/570 |
|---|---|---|---|
| 443026 | 11/1974 | United Kingdom | 260/570 |

OTHER PUBLICATIONS

Olah, "Friedel-Crafts and Related Reactions," vol. I, pp. 29, 329-331, 338-341.
Brittles et al., "J. Polymer Science," Part A-2, pp. 1847-1849, 1854, 1858, (1964).
Tanabe, "Solid Acids and Bases Their Catalytic Properties," pp. 1-3, 5-7, 73-75, (1970).
Robertson, "Clay Minerals Bulletin," 1, (2), pp. 47-54, (1948).
Girdler Chemical Co., "Technical Work Sheet," G. C. 1273.

*Primary Examiner*—Robert V. Hines
*Attorney, Agent, or Firm*—D. B. Little

[57] ABSTRACT

Diphenylamine is reacted with styrene in the presence of a base modified acid clay catalyst to improve yields of the p-styrenated diphenylamine (DPA), particularly the distyrenated DPA. Fuller's Earth exemplifies the clay, while KOH exemplifies the base. The highly p-styrenated diphenylamine is an active antioxidant with low volatility.

7 Claims, No Drawings

BASE MODIFIED CATALYSIS IN THE STYRENATION OF DIPHENYLAMINE

This is a continuation of application Ser. No. 840,440 filed Oct. 7, 1977 now abandoned.

This invention relates to a process for preparing styrenated diphenylamine. More particularly it relates to a process for preparing large yields of p-styrenated diphenylamines.

The prior art reveals the preparation of alkylated amines and the use of the products as antioxidants, e.g., see U.S. Pat. Nos. 3,505,225; 3,452,056; 3,649,690; 2,943,112; German 895,973; U.S. Pat. Nos. 2,943,112; 3,505,225; 3,072,603; 2,776,994; 3,714,257; 3,714,258; 3,496,230. High yields of product are obtained in styrenating or α-methyl styrenating diphenylamine (DPA) using clay catalysts. Although high levels of para substitution can be obtained routinely when alkylating DPA with α-methyl styrene (AMS) using clay catalysts, low amounts of para substitution can result when one attempts to react styrene, rather than AMS, with DPA using clay catalysts. Others have increased yields of p-substituted DPA (see Application Ser. No. 569,516, filed Apr. 18, 1975 and Application Ser. No. 746,650, filed Dec. 2, 1976). A process is desired which would provide increased amounts of p-styrenated DPA, particularly di-p-substituted DPA, since higher levels result in increased antioxidant effectiveness and decreased volatility.

An object of the present invention is to provide a method in which either acid activated or naturally active acid clay catalysts can be modified by base to yield a styrenated DPA product containing an increased yield of p-substituted DPA. Another object is to provide a method of preparing high levels of 4,4'-distyryldiphenylamine.

The objects of the present invention are accomplished by reacting a combination of diphenylamine and styrene in the presence of a nonacid activated (i.e., naturally active) or acid activated acidic clay catalyst modified by the addition of small amounts of basic material at a temperature of from 170° C. to 300° C., preferably 185° C. to 275° C., and most preferably 200° C., wherein 1 to 3 mols of styrene are charged per 1 mol of diphenylamine, preferably 2.0 to 2.5 mols of styrene per mol of diphenylamine.

The method of modifying the clay catalyst with the base is not critical. For example, it can be accomplished by adding the base to a mixture of diphenylamine and clay catalyst prior to styrene addition or by premixing the base with the clay catalyst and adding this premix to diphenylamine followed by styrene addition.

The reaction may be run with or without solvent. If a solvent is used it must be inert and compatible with the reaction temperatures used. Examples of solvents are p-cymene and p-diisopropylbenzene. It is preferred to run the reaction without solvent since no recovery or separation is required.

The reaction may be accomplished batchwise or on a continuous basis at various pressures, including atmospheric pressure.

The reaction product is an effective antioxidant which can be used in the stabilization of materials subject to oxidation degradation, particularly diene rubbers such as butadiene/nitrile rubbers, at elevated temperatures.

It is theorized that the base modifier changes the surface acidity of the clay catalyst. For the non-acid washed, naturally active clays (no residual acid present), the base addition apparently alters inherent surface acidity, while base addition to acid activated clays may both neutralize some of the residual acid (KSF, for example, contains about 6 percent sulfuric acid) and alter the inherent surface acidity as well. The catalysts can be water extracted and pH measure used to determine residual acid levels. It is believed that changing surface acidity by base modification is at the crux of this invention.

Acid activated clays are clays which are treated with acid, e.g., $H_2SO_4$, to activate what would normally be a clay with low activity (say for alkylation reactions). The protons of the acid will replace any cationic materials present, e.g., $K^+$, $Na^+$, $Ca^{++}$. The clay can then be washed free of any residual acid and still be active because of the protons that replaced the cationic metals. At reaction temperatures used for clay catalysts it is theorized that these protons catalyze the reaction.

For non-acid washed, naturally active clays, e.g., Fuller's Earth, no acid treatment is necessary to activate the clay.

The acidic clay catalysts are well known in the art. They can be acid treated (activated) clays or untreated, that is, naturally active clays. They normally contain major amounts of aluminum hydrosilicate, their general composition being of the type $M[AlO_2]x(SiO_2)y].ZH_2O$ where M is metal cation selected from $K^+$, $Na^+$, $Ca^{+2}$, $Fe^{+2}$, $Fe^{+3}$, etc. and Z is the number of mols of water of hydration. The activity of the clay catalyst is dependent upon several factors such as the particle size, moisture content, surface area, acidity, etc.

A typical clay composition would be as follows with the more typical ranges enclosed within the parenthesis.

| Component | Weight Percent |
|---|---|
| $SiO_2$ | 50–80 (70–75) |
| $Al_2O_3$ | 5–30 (15–20) |
| $Fe_2O_3$ | |
| MgO | 0–20 (8–15) |
| CaO | |
| $K_2O$ | |
| Residual Acid | 0–10 (0–10) |

Examples of these catalysts are the acid activated Montmorillonite catalysts of the K series produced by Chemetron Corporation, and activated clay adsorbents of Filtrol Corporation. Fuller's Earth is an example of a naturally active clay.

The amount of catalyst is not critical to the practice of the invention. Naturally, as with any process, the catalyst level can be reduced to such a low level that the reaction rate will either be extremely low or nil. As a guideline, but not a limitation, at least 6 parts by weight of catalyst should be used per 100 parts by weight of diphenylamine. More preferably at least 10 parts by weight should be used. There is no upper limit on catalyst level. For example, 100 parts of catalyst or more can be used. However, merely as a practical matter, the amount of catalyst should not exceed 20 or 25 parts.

The clay catalysts need not be preconditioned, e.g. water removed, in order for the claimed catalyst system to be useful, although preconditioned catalysts can be used.

A typical base is one having a pKa ≧3, relative to water (see Advanced Organic Chemistry: Reactions, Mechanisms and Structure, Jerry March, McGraw-Hill (1968) pages 219-221; also see Perrin, "Dissociation Constants of Organic Bases in Aqueous Solution", Butterworth & Co., Ltd., London, 1965.

The organic and inorganic bases are illustrated by but not limited to the following:
Potassium hydroxide
Tetraethylammonium hydroxide
Trimethylbenzylammonium hydroxide
ANGA-542 ion exchange resin
Aniline
(1,8-bis-dimethylamino)-naphthalene
Diethylenetriamine
Triethylamine Examples 1 and 3 illustrate the preparation of styrenated DPA using an acid clay catalyst but no base modifier.

Examples 2 and 4 illustrate the preparation of styrenated DPA using an acid clay catalyst with a base modifier. Examples 2 and 4 illustrate but do not limit the practice of the present invention.

EXAMPLE 1 (Naturally Active Clay)

A mixture of diphenylamine (75 g., 0.44 m.) and 4.6 g. Bentolite L (catalyst grade) clay catalyst (6 wt. % based on diphenylamine) was heated to 220° C. followed by the addition of styrene (92.3 g., 0.88 m.) over 2.0 hours. The reaction mixture was heated at 220° C. for 1.0 hour more, followed by removal of the clay catalyst by hot filtration. 49.1 wt. % of 4,4'-distyryl-diphenylamine was found.

EXAMPLE 2 (Naturally Active Clay + Base)

A mixture of diphenylamine (75 g., 0.44 m.) 46 g. Bentolite L (catalyst grade) clay catalyst and 0.25 wt. % Triton B (based on diphenylamine) was heated to 220° C. followed by the addition of styrene (92.3 g., 0.88 m.) over 2.0 hours. The reaction mixture was heated at 220° C. for 1.0 hour more, followed by removal of the clay catalyst by hot filtration. 69.8 wt. % 4,4'-distyryl-diphenylamine was found.

A comparison of Examples 1 and 2 illustrates the tremendous improvement in selective yield through the use of a base modifier.

EXAMPLE 3 (Acid Activated Clay)

A mixture of diphenylamine (75 g., 0.44 m.) and 4.6 g. KSF clay catalyst (6 wt. % based on diphenylamine) was heated to 220° C. followed by the addition of styrene (92.3 g., 0.88 m.) over 2.0 hours. The reaction mixture was heated at 220° C. for 1.0 hour more, followed by removal of the clay catalyst by hot filtration. 24.1 wt. % 4,4'-distyryldiphenylamine was found.

EXAMPLE 4 (Acid Activated Clay + Base)

A mixture of diphenylamine (75 g., 0.44 m.), 4.6 g. KSF clay catalyst (6 wt. % based on diphenylamine) and 0.25 wt. % Triton B (based on diphenylamine) was heated to 220° C. followed by the addition of styrene (92.3 g., 0.88 m.) over 2.0 hours. Triton B is a 40% solution of benzyltrimethylammonium hydroxide in methanol. The reaction mixture was heated at 220° C. for 1.0 hour more, followed by removal of the clay catalyst by hot filtration. 38.5 wt. % 4,4'-distyryldiphenylamine was found.

Again a base modifier increased selective yield, this time with an acid activated clay.

Reactions were run according to the conditions in Example 2 using other base modifiers and clay catalysts. The results are recited in Tables I and II.

The following abbreviations are used in Tables I and II:
P—weight % mono-p-styrenated DPA
PP—weight % di-p-styrenated DPA
P/O—ratio of para substitution to ortho substitution
Sty/DPA—molar ratio of reacted styrene to reacted DPA The effectiveness of the base in modifying the reaction is dependent on the type of base used. All bases are effective, some being more effective than others. The effective concentration of each base must be established as illustrated in Tables I and II. In general the stronger bases which would be expected to be soluble in the reaction medium are the most effective.

TABLE I

Clay Catalyst: Bentolite L (Cat. Grade)

| Base (wt. %) | P | PP | P/O | Sty/DPA | Footnote |
|---|---|---|---|---|---|
| None | 8.8 | 49.1 | 3.74 | 2.00 | |
| KOH (0.1) | 10.9 | 49.8 | 4.60 | 1.95 | (1) |
| KOH (0.2) | 9.5 | 53.9 | 4.70 | 1.97 | |
| KOH (0.53) | 11.2 | 60.6 | 6.16 | 1.94 | |
| KOH (0.7) | 11.0 | 62.5 | 6.41 | 1.94 | |
| KOH (1.0) | 40.7 | 33.8 | 12.1 | 1.39 | (2) |
| DETA (0.0125) | 8.3 | 53.7 | 4.16 | 1.99 | (3) |
| DETA (0.025) | 8.8 | 58.0 | 5.03 | 1.98 | |
| DETA (0.05) | 10.5 | 64.5 | 7.09 | 1.92 | |
| DETA (0.1) | 27.1 | 50.9 | 9.45 | 1.65 | |
| Et$_3$N (0.05) | 9.5 | 59.9 | 5.47 | 1.96 | (4) |
| Et$_3$N (0.1) | 8.3 | 63.6 | 6.53 | 1.97 | |
| Et$_3$N (0.2) | 38.2 | 34.9 | 6.95 | 1.46 | (5) |
| Triton B (0.05) | 7.4 | 59.0 | 5.00 | 1.99 | (6) |
| Triton B (0.1) | 6.7 | 69.8 | 7.62 | 1.97 | |
| Triton B (0.2) | 8.6 | 68.2 | 8.84 | 1.93 | |
| Triton B (0.3) | 24.5 | 57.7 | 16.4 | 1.66 | |
| Et$_4$NOH (0.05) | 9.5 | 59.9 | 5.47 | 1.96 | (7) |
| Et$_4$NOH (0.1) | 8.2 | 63.0 | 6.05 | 1.99 | |
| Et$_4$NOH (0.2) | 9.3 | 69.5 | 8.80 | 1.94 | |
| Et$_4$NOH (0.3) | 37.7 | 43.1 | 18.1 | 1.46 | (8) |
| ANGA-542 (0.25) | 7.6 | 59.6 | 5.20 | 1.99 | (9) |
| AGA-542 (0.5) | 8.0 | 70.4 | 9.03 | 1.94 | |
| ANGA-542 (1.0) | 13.3 | 71.4 | 14.9 | 1.83 | |
| ANGA-542 (1.52) | 24.7 | 61.3 | 24.5 | 1.67 | (10) |

(1) Added as a 50% aq. KOH solution.
(2) Required 3.0 hrs. to add styrene to maintain 220° C.
(3) DETA = diethylenetriamine (Aldrich).
(4) Et$_3$N = triethylamine (Aldrich).
(5) Required 5.5 hrs. to add styrene to maintain 220° C.
(6) Triton B = benzyltrimethylammonium hydroxide (Aldreich), added as a 40% solution in methaol.
(7) Et$_4$NOH = tetraethylammonium hydroxide (Aldrich), added as a 20% solution in water.
(8) Required 4.75 hrs. to add styrene to maintain 220° C.

TABLE II

Clay Catalyst: Clarolite T-30

| Base (wt. %) | P | PP | P/O | Sty/DPA | Footnote |
|---|---|---|---|---|---|
| None | 14.5 | 48.9 | 4.22 | 1.91 | |
| Aninline (0.1) | 12.1 | 47.0 | 3.92 | 1.95 | |
| Aniline (1.0) | 13.3 | 54.0 | 5.50 | 1.90 | |
| Aniline (5.0) | 21.3 | 55.9 | 9.26 | 1.73 | |
| Proton Sponge (0.05) | 11.2 | 57.4 | 5.48 | 1.95 | 1 |
| Proton Sponge (0.1) | 14.0 | 61.4 | 8.25 | 1.87 | |
| DETA (0.025) | 12.2 | 55.1 | 5.19 | 1.93 | |
| DETA (0.05) | 16.6 | 53.7 | 6.40 | 1.81 | |
| Triton B (0.1) | 13.8 | 62.0 | 7.51 | 1.88 | |
| ANGA-542 (0.51) | 11.8 | 64.1 | 8.60 | 1.89 | |

[1]Proton Sponge = 1.8-bis(dimethylamino)naphthalene (Aldrich)

As demonstrated in Tables I and II, the amount of para-substitution continues to increase as the level of base modifier increases (see P/O) without sacrificing the reaction rate (see Sty/DPA). There is a level of base modifier, however, at which the level of PP substitution decreases and the reaction rate also decreases. This point can be determined by routine experimentation as demonstrated in Tables I and II for each base used.

While certain representative embodiments and details have been shown for the purpose of illustrating the invention it will be apparent to those skilled in this art that various changes and modifications may be made therein without departing from the spirit or scope of the invention.

I claim:

1. An improved process for producing a styrenated diphenylamine comprising reacting diphenylamine and styrene in the presence of an acidic clay catalyst, wherein the improvement comprises modifying the acidic clay catalyst by the addition of a base to the system.

2. The process improvement according to claim 1 wherein the reaction occurs at a temperature of from 170° C. to 300° C.

3. The process improvement according to claim 1 wherein molar ratio of styrene to diphenylamine is from 1:1 to 3:1.

4. The process improvement of claim 1 wherein the reaction occurs at a temperature of from 185° C. to 275° C. and the molar ratio of styrene to diphenylamine is from 2:1 to 2.5:1.

5. The process improvement as recited in claim 3 wherein the amount of catalyst used is from 6 to 25 parts by weight per one hundred parts by weight of diphenylamine.

6. The process improvement as recited in claim 5 wherein the base has a pKa $\geq 3$, relative to water.

7. The process improvement as recited in claim 6 wherein the base is selected from the group consisting of potassium hydroxide, tetraethylammonium hydroxide, trimethylbenzylammonium hydroxide, aniline, (1,8-bis-dimethylamino)-naphthalene, diethylenetriamine, triethylamine and polystyrenealkyl quaternary amine ion exchange resin.

* * * * *